United States Patent [19]

Archibald

[11] 4,267,842
[45] May 19, 1981

[54] MICRO-ARTERIAL SLEEVE-GRIP

[76] Inventor: Steven L. Archibald, 1816 F. St. #7, Sacramento, Calif. 95814

[21] Appl. No.: 56,133

[22] Filed: Jul. 9, 1979

[51] Int. Cl.³ .............................................. A61B 17/11
[52] U.S. Cl. ................................. 128/334 R; 285/398
[58] Field of Search ....................... 128/334 R, 334 C; 285/398, 371, 419

[56] References Cited

U.S. PATENT DOCUMENTS

| 1,329,121 | 1/1920 | Hachman | 285/371 |
| 2,737,402 | 3/1956 | De Frumerie et al. | 285/398 |
| 3,155,095 | 11/1964 | Brown | 128/334 C |
| 3,357,432 | 12/1967 | Sparks | 128/334 C |
| 3,435,823 | 4/1969 | Edwards | 128/334 C |
| 3,683,926 | 8/1972 | Suzuki | 128/334 R |

*Primary Examiner*—Norman Yudkoff
*Attorney, Agent, or Firm*—Blair, Brown & Kreten

[57] ABSTRACT

Disclosed herein is a device for joining together separated arteries, lumen or the like. The device includes an innertube of substantially cylindrical configuration having end portions which taper somewhat and terminate at opposed extremities in a fine feathered end. Attached to the center cylindrical portion, is a sleeve grip mechanism which extends over the tapered portions as well so that when an artery is slidably disposed over the tapered portions of the innertube, the sleeve grip can wrap around the central cylindrical portion and the tapering portion, and opposed ends of the sleeve grip can be fastened together to securely affix the dissociated artery to the central cylindrical portion thereby repairing the artery and allowing the flow of blood to recommence therethrough.

10 Claims, 4 Drawing Figures

MICRO-ARTERIAL SLEEVE-GRIP

BACKGROUND OF THE INVENTION

The traditional techniques associated with rejoining severed tubular organs in a body comprises sewing together the severed area with very fine thread that is approximately three times finer then a human hair, performed with a magnifying device, so that the work can accurately monitored. It should be apparent, that with precision work of this nature, a substantial amount of time is required to join together two such articles, and in situations such as these, time is essential in effecting the rejoining since an area deprived of blood can suffer irreversible damage. The time demands become substantially more aggravated when the nature of the injury is quite extensive, and plural arteries require joining, for example when a hand is severed. Currently, an excess of twenty hours is required to rejoin a severed hand, and therefore the hand to be joined should be preserved by packing in ice or the like so as to increase the likelihood that the rejoining of the hand will suffer from a minimal amount of irreversible damage.

SUMMARY AND OBJECTS OF THE INVENTION

Accordingly, the ensuing detailed invention is directed to an apparatus for reducing the amount of time for joining severed arteries and other types of lumen so that vital blood flow can be caused to pass through the arteries in the shortest amount of time, thereby decreasing the likelihood of damage due to blood deprivation.

It is an object of this invention therefore to provide a device of the character described above which can be quickly and safely used to join severed arteries.

A further object contemplates providing a device which when inserted will not be rejected by the body and will be of small enough dimensions that it will not impair motion.

A further object contemplates providing a device of the character described above which is suitable for arteries of various dimensions located in various parts of the body.

A further object contemplates providing a joining device which once inserted is capable of being retained in the body substantially indefinitely.

These and other objects will be made manifest when considering the following detailed specification when taken in conjunction with the appended drawings.

DESCRIPTION OF THE PREFERRED EMBODIMENTS

Figure 1:
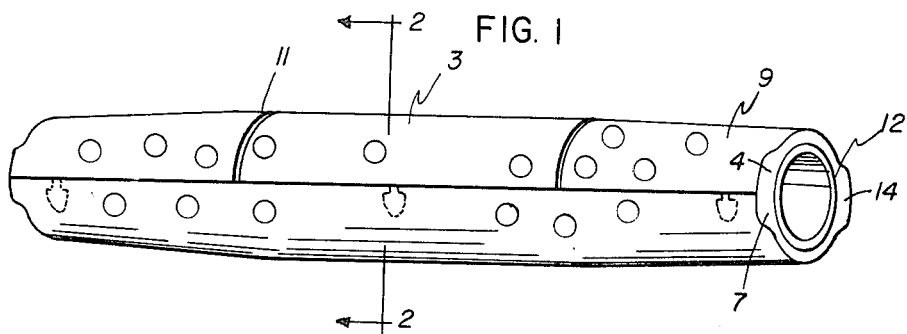
FIG. 1 is a perspective view of the device according to the present invention.

Referring to the drawings now, wherein like reference numerals refer to like parts throughout the several figures, reference numeral 10 is directed to the joining device according to the present invention.

This joining device may be regarded as having an innertube (intra-catheter) 1 of substantially cylindrical configuration. Extending from both ends of the innertube or cylinder 1 is a conically tapered end portion 2 having termini at opposed extremities of the innertube forming truncated ends 12. It is desired that these truncated ends 12 have a feathered edge so that the thickness thereof is minimial. As shown in the drawings, the severed arteries A are caused to slide over the conical portions 2 up to the cylindrical center portion of innertube 1.

Figure 2:
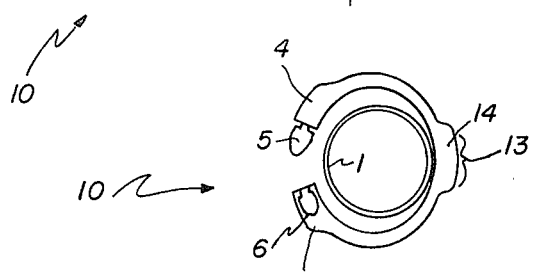
FIG. 2 is a sectional view taken along lines 2—2 of FIG. 1 wherein the latching mechanism is as yet unhooked.

In order to insure that the arteries A thus disposed will not become dissociated from the conical portions 2, an overlying sleeve grip 21 is provided. As best seen in FIG. 2, the sleeve grip 21 has a central portion 3 which is preferably attached to the innertube 1 and free end portions 9 which are caused to overlie the tapered end portions 2 of the innertube 1. Desirably, the sleeve grip 21 is formed from the same material as the innertube 1, and etched teflon has been found to be a suitable substance since it has a very low likelihood of rejection by the body. The center portion 3 of the sleeve grip 21 has a generally rectangular configuration and dimensions such that when it is rolled over the innertube 1, it completely envelops same. The free end portions 9 have a taper so that they may securely engage the tapered end portions 2 of the innertube 1 and affix the artery firmly thereto. To this end, slits 11 are disposed on opposed sides of the central portion 3, and fenestrations 8 are disposed along the entire sleeve grip 21. The marginal top and bottom edge portions of the sleeve grip 21 are provided with thickened areas 4 and 7 which serve to support and house the fastening devices so that when the sleeve grip 21 is rolled over the innertube 1 and tapered portions 2, it can be locked over the arteries A. As shown in FIG. 2, male fasteners 5 are provided along one thickened area 4, and a spade type configuration is found to be a suitable and reliable fastening device. The opposed thickened area 7 is provided with recesses 6 having a spade like configuration so as to receive the male fasteners 5. The area 13 that joins the innertube 1 to the central portion 3 of the sleeve grip 21 has a thickened portion 14 for additional structural rigidity, somewhat similar to the thickened areas 4 and 7 along edge portions of the sleeve grip 21.

In use and operation, a suitable example would take the following form. The intra-catheter 1 would be approximately 5 millimeters long having an inside diameter of 1 millimeter. Formed from teflon, the device 10 would retain the desirable properties of low rejection factor, minimal tissue disturbance, and at the same time remain pliant. The resiliency and pliancy should be sufficient to withstand deformation by the sleeve grip 21. The thickness of the wall of the innertube 1 should be adjusted to compensate for the overall tapering and to allow a 1 mm flow throughout the lumen or passageway. The wall thickness should taper to a very fine feather edge at truncated ends 12, and the backwall of the innertube 1 is attached to the sleeve grip 21 for 2 mm in length leaving 1½ mm of each tapered portion to allow the artery to slide thereover after it has been properly dilated.

The fenestrated sleeve grip 21 will also be 5 mm in length and conforming to the taper of the end portions 9 allowing slightly less space between itself and the innertube 1 than the thickness of the arterial wall (approximately 1 mm). The dimension and number of the fenestrations 8 can be adjusted to permit the desired tension so as to produce a "Chinese finger lock" effect on the arteries A when same is under a pulling stress. The male fasteners 5 can be formed from teflon and the female joiners could be made of silastic thick enough to permit a snap coupling with the male fasteners 5.

Of course the dimensions and materials of this prosthesis device are merely illustrative since it is contemplated that various dimensions for this sleeve grip 21 and innertube 1 be provided to accommodate arteries A of various dimensions. It is also contemplated that the sleeve grip 21 and the innertube 1 can be of any desired length to permit anastomosis of vessels and arteries that have been avulsed for several millimeters.

Figure 4:
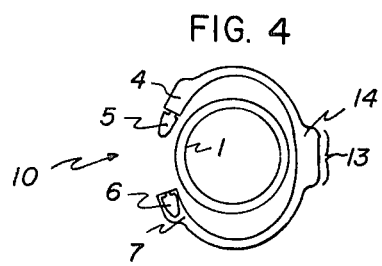
FIG. 4 details a sectional view similar to FIG. 2 revealing an alternative embodiment.
Figure 3:
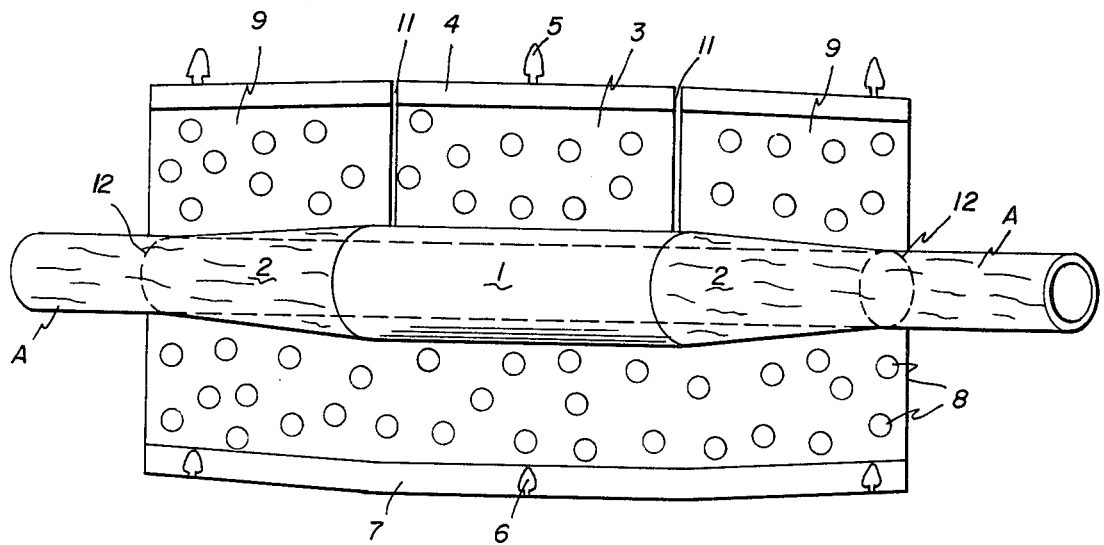
FIG. 3 is a perspective view of the apparatus according to the present invention in which the sleeve grip and inner cylinder are opened for inspection.

Further it should be clear from FIG. 4 that the sleeve grip 21 may not be joined initially to the innertube 1, since these components can be more readily manufactured separately and joined later.

Having thus described the invention, it should be apparent that numerous structural modifications are contemplated as being part of this invention as specified hereinabove and as defined hereinbelow by the claims.

What is claimed is:

1. A device for joining arteries and the like comprising an innertube having a central portion of substantially uniform cross section, said innertube having a central opening therethrough which terminates at opposed extremities thereof to open ends, and having end portions on opposite sides of said central portion, said innertube end portions having a generally tapering cross section adapted to receive an artery or vein thereover, and one-piece gripping means having a central portion movable into overlying engagement with said innertube central portion and oppositely disposed, tapering end portions movable independently of said gripping means central portion into overlying retaining engagement with an artery disposed on said innertube end portions.

2. The device of claim 1 in which a terminal portion of each of said innertube end portions is provided with a fine feathered edge.

3. The device of claim 2 in which said gripping means includes a blank of material which can be wrapped over said innertube.

4. The device of claim 3 in which said blank is affixed to said innertube central portion along the central area thereof.

5. The device of claim 4 in which said blank is provided with fenestrations.

6. The device of claim 5 in which said blank is provided with a reinforced area at the juncture with said innertube central portion.

7. The device of claim 6 in which said gripping means is provided with reinforced areas extending along the marginal extremities of said blank parallel to said innertube central portion.

8. The device of claim 7 in which said reinforced areas are provided with male and female fasteners so that said gripping means can overlie said innertube central and end portions and be fastened.

9. The device of claim 8 in which said male and female fasteners comprise spade-shaped lugs and recesses.

10. The device of claim 9 in which said gripping means central portion is separated from said gripping means end portions by means of slits.

* * * * *